United States Patent [19]
Orth et al.

[11] 3,954,891
[45] May 4, 1976

[54] METHOD OF MAKING SUBSTITUTED HYDROQUINONES

[75] Inventors: Winfried Orth, Hasloch, Pflaz; Manfred Maurer, Frankenthal, Pfalx, both of Germany

[73] Assignee: Rutgerswerke Aktiengesellschaft, Frankfurt, Germany

[22] Filed: Nov. 27, 1972

[21] Appl. No.: 309,769

[30] Foreign Application Priority Data
Dec. 7, 1971  Germany.......................... 2160599

[52] U.S. Cl.......................... 260/621 H; 260/396 R
[51] Int. Cl.².................. C07C 37/00; C07C 37/06
[58] Field of Search............ 260/621 H, 396 R, 625

[56] References Cited
UNITED STATES PATENTS

| | | |
|---|---|---|
| 2,259,936 | 10/1941 | Jung.............................. 260/621 H |
| 2,608,561 | 8/1952 | Monnberg et al............... 260/396 R |
| 2,730,535 | 1/1956 | Gaydasch et al................ 260/396 R |
| 3,723,541 | 3/1973 | Schuster et al.................. 260/621 H |
| 3,795,708 | 3/1974 | Rappen et al................... 260/621 H |

FOREIGN PATENTS OR APPLICATIONS

| | | |
|---|---|---|
| 7,011,586 | 2/1971 | Netherlands..................... 260/621 H |
| 595,514 | 12/1947 | United Kingdom............. 260/621 H |

*Primary Examiner*—Norman Morgenstern
*Attorney, Agent, or Firm*—Jerry Cohen; Charles Hieken

[57] ABSTRACT

Substituted quinones are catalytically hydrogenated in the presence of a mixture of (1) low unbranched alcohols and (2) hydrocarbons which are inert and fluid under the conditions of the hydrogenation reaction and which may be aromatic, aliphatic or cycloaliphatic to economically produce corresponding substituted hydroquinones of high purity and low discoloration and in high yields thereof.

18 Claims, No Drawings

METHOD OF MAKING SUBSTITUTED HYDROQUINONES

BACKGROUND OF THE INVENTION

The invention concerns a process for the manufacture of hydroquinones and more particularly 2, 3, 5 trimethylhydroquinones through the catalytic reduction of the corresponding quinone with hydrogen at low pressures and temperatures.

German patent application publication 1956381 teaches forming hydroquinone derivatives, for example, 2, 3, 5 trimethylhydroquinone through catalytic hydrogenation, using copper chromite catalytic agents, of the corresponding quinone in solution at elevated pressures (80–150 atmospheres) and temperatures (50°–150°C, or higher). As a solvent one can use alcohol (for example, methanol, ethanol, etc.), ether (for example, dioxane) or water. The processing at elevated pressures and temperatures requires complex equipment. The process has the further drawback that the end products are not pure and must be purified through recrystallization in the presence of a stabilizer.

German patent 683908 teaches catalytic hydrogenation of trimethyl-p-quinone in the presence of an organic solvent and a palladium catalyst, to trimethylhydroquinone. Solvents that can be used are ether, glacial acetic acid, dilute acetic acid, toluol-alcohol and alcohol, apparently ethanol. In working in accordance with the teaching of this patent with methanol or ethanol one obtains in part very impure end products. These show strong coloration even if a filtrate is separated from the catalyst in the absence of atmospheric oxygen, and evaporated as it is passed through carbon dioxide, as called for in the patent.

In particular during hydrogenation in reaction vessels made of stainless steel one obtains exceptionally strongly colored trimethylquinone caused by the formation of black quinhydrone which makes it impossible to use the end product for further processing as for example in the manufacture of vitamin E. If one uses one of the other solvents called for in patent 683908, then the trimethylhydroquinone resulting from the hydrogenation precipitates and the catalyst becomes encrusted and enclosed and therefore ineffective shortly after starting the process. The same is true in the utilization of aromatic hydrocarbons, for example toluol, aliphatic or cycloaliphatic hydrocarbons alone or mixed with each other, for example, in hexane ligroine and cyclohexane in higher alcohols, for example n-heptanol. Under these circumstances, the high boiling solvents are separated from the end product only with the greatest difficulty.

German patent application publication 1940386 carries out the hydrogenation of trimethyl-p-quinone with hydrogen to trimethylhydroquinone in the presence of an alcohol of 3–5 carbon atoms and at a temperature of 60°–180°C. In this way, the autooxidation, as indicated by the coloration of the end product, is said to be greatly reduced, particularly if one uses branched alcohols of the described type as solvents. However the drawbacks of this process are that the hydrogenation, in contrast to patent 683908, must be carried out at elevated temperatures and that on the basis of the relatively high solubility of the end product in the alcohol used, the starting brine must be used several times. Thereby the impurities are continually enriched, which eventually can lead to a reduction of quality of the trimethylhydroquinone through cocrystallization of by-products, which should particularly be avoided.

It is therefore an important object of the present invention to provide an economical process which will not be characterized by the cited drawbacks and which will lead in particular to very pure and light hydroquinones.

SUMMARY OF THE INVENTION

The process for the fabrication of a substituted hydroquinone, in particular 2, 3, 5 trimethylhydroquinone comprises the catalytic hydrogenation of the corresponding quinone at normal pressures or slightly elevated pressures and at room temperature or slightly elevated temperatures in the presence of a mixture of inert aromatic, aliphatic or cycloaliphatic hydrocarbon solvent and a low, non-branched, aliphatic alcohol in a volume ratio of inert hydrocarbon to alcohol of at least 1 to 1.4 between 0° and 60°C, preferably at 20°–25°C.

The inert hydrocarbon must be fluid under the conditions of the reactions, and is preferably selected from the class consisting of toluene, benzene, hexane, cyclohexane and ligroine. The volume ratio relationship of the inert hydrocarbon solvent to the low alcohol is selected in such a way that the resulting reaction product remains dissolved in the solvent mixture during the reaction. Generally that is the case for a volume relationship of hydrocarbon to alcohol in accordance with Table 1.

Table 1

|  | Methanol | Ethanol | Propanol | Isopropanol |
| --- | --- | --- | --- | --- |
| Toluene | 1:1 | 1:1.45 | 1:1.7 | 1:1.45 |
| Benzene | 1:1 | 1:1.45 | 1:1.7 | 1:1.45 |
| Hexane | — | 1:1.45 | 1:2.0 | 1:2.0 |
| Cyclohexane | — | 1:1.45 | 1:2.0 | 1:1.85 |
| Ligroine | — | 1:1.45 | 1:2.3 | 1:2.0 |

In this way the catalyst can be separated from a homogeneous solution after the reaction and the hydroquinone form can be precipitated through the addition of water. In contrast to the process in accordance with the German patent 683908 the separation of the catalyst can be carried out in the presence of atmospheric oxygen so that the need for expensive equipment is thereby avoided.

As catalysts, all known hydrogenation catalysts can be used, e.g. Raney nickel, Raney cobalt, platinum, palladium, ruthenium, rhodium and rhenium catalysts. Preferably they are used as carrier catalysts in the form of 1–5 weight percent catalyst in reference to the carrier material. Examples of usable conventional carriers are carbon and aluminum oxide. In general, one adds the catalyst in an amount of 0.1 to 3.0, preferably 1.5 weight percent in reference to the quinone. In the case of the Raney catalyst, one preferably uses about 10 weight percent in reference to the quinone.

The catalysts can be used several times in sequence. For example, it has been observed that when using the palladium catalyst on carbon (5%) there is no noticeable decrease in activity after the tenth use. The reaction is exothermic and takes place in the region of 0° to 60°C preferably at room temperature (20°–25°C). The quinone is hydrogenated for such a period of time until hydrogen takeup stops of its own accord and in this way the theoretical amount of hydrogen is taken up. The hydrogenation takes place in the region of 1 to 50 atmospheres, preferably at 1 to 8 atmospheres; it can also be carried out continuously, e.g. in reactor tubes or cascades.

For the production of 2, 3, 5 trimethylquinone according to the German publication 1932362, solutions of the quinone in aromatic, aliphatic or cycloaliphatic hydrocarbons are particularly suitable. One adds to these solutions exactly such amount of low alcohol as for example methanol, ethanol, propanol or isopropanol that the end product resulting from the hydrogenation remains in solution. The necessary relationship of the quinone containing solution to alcohol is in accordance with Table 1 above.

The use of such trimethylquinone solutions is particularly economical, because in this way the quinone of itself does not need to be isolated and purified, but it can be hydrogenized in the solution to the end product immediately after its formation.

After completing the takeup of hydrogen, half of the solution mixture is distilled off and the remainder is replaced with an equal amount of 0.5% sodium sulfite solution. In this way the hydroquinone is precipitated as a light precipitate. The yield lies above 90% of the theoretical value. The inert solvent material which separates itself in the filtrate can be re-used in a particularly economical way in the fabrication of new quinone solutions, as for example, in accordance with the German publication 1932362.

Trimethylhydroquinone and 2, 6 dimethylhydroquinone are, for example, important intermediate products for the manufacture of tocopherol (vitamin E), the use of which is described in Ullmann's Encyclopedia of Technical Chemistry Vol. 18, p. 241 (1967).

DETAILED DESCRIPTION OF PREFERRED EMBODIMENTS

The following non-limiting example illustrates the practice of the inventive process.

EXAMPLE 1

350ml, of a toluene solvent, quinone solute, solution, which contained 141.5 grams (0.95 mole) trimethyl-p-quinone, were displaced with 1.5 grams palladium catalyst (2.5%) on carbon and 350 ml methanol in a one-liter stirring pressure reaction vessel of stainless steel. Then the vessel was flushed with nitrogen and then the modified solution was hydrogenized by admitting hydrogen to the vessel and establishing a hydrogen pressure of 4–8 atmospheres and a temperature of 20° to 25°C and stirring until the end of the hydrogen takeup. The duration of hydrogenation was 30 to 40 minutes. Then the hydrogenated material was separated from the catalyst (which was usable for the next charge) and half of the solvent material was distilled off. Into the remainder of the solution 325 ml 0.5% sodium bisulfite solution was dripped while continuously stirring while sucking off liquid from the precipitated trimethylhydroquinone. The precipitate was washed first with 125 ml toluene, then with 250 ml 0.5% sodium bi-sulfite solution and dried in vacuum at 70°C. The toluene which separated off in the filtrate was recycled back into the quinone fabrication. This produced 136 grams of trimethylhydroquinone, equal to approximately 94.3% of the theoretical value. The melting point of the substance produced was 169°–170°C.

EXAMPLE 2

360 ml of a toluene solvent, quinone solute, solution containing 127.5 grams (0.85 mole) trimethyl-p-quinone, were displaced with 15 grams Raney-Nickel and 360 ml methanol in a one-liter stirring pressure reactor vessel of stainless steel. This was hydrogenated at 50°C under a pressure of 30–50 atm. and worked further as described in Example 1.

The yield of trimethylhydroquinone was 122.5 grams which is equal to approximately 95% of theoretical yield. The melting point of the product was 169°–170°C.

EXAMPLE 3

A solution of 237 grams (1.58 mole) trimethyl-p-quinone, dissolved in 400 ml cyclohexane, was displaced with 2.4 grams platinum catalyst on carbon (approximately 5%) and 1120 ml propanol in a two-liter stirring pressure reactor vessel of stainless steel and hydrogenated and worked as in Example 1. The yield of trimethylhydroquinone was 225 grams, (equal to approximately 93.8% of theoretical). The melting point was 169°–170°C.

EXAMPLE 4

A solution of 225 grams (1.5 mole) trimethyl-p-quinone, dissolved in 375 ml hexane, was displaced with 1 gram of rhodium catalyst (5% on carbon) and 750 ml ethanol in a one-liter stirring pressure reactor vessel and hydrogenated and worked as in Example 1. The yield was 219 grams, equal to approximately 96% of theoretical and the melting point was 169°–170°C.

EXAMPLE 5

A solution of 300 grams (2 moles) trimethyl-p-quinone, dissolved in 500 ml benzene, was displaced with 1.5 grams ruthenium catalyst (5% on carbon) and 700 ml methanol in a two-liter stirring pressure reactor vessel and hydrogenated at room temperature at a pressure of 4–8 atmospheres until the end of hydrogen takeup and worked as described in Example 1. The yield was 295 grams, equal to approximately 97% of theoretical and the melting point was 169°–170°C.

EXAMPLE 6

A solution of 136 grams (1 mole) 2,6 dimethylquinone, dissolved in 250 ml toluene, was displaced with 350 ml methanol and 1.0 grams rhodium catalyst (3% on aluminum oxide) and hydrogenated at room temperature and normal pressures to the end of hydrogen takeup. The process was carried out as in Example 1 and the yield of 2,6 dimethylhydroquinone was 133.5 grams, equal to approximately 96.7% of theoretical and the melting point was 150°–152°C.

EXAMPLE 7

A solution of 300 grams (2 moles) of trimethyl-p-quinone, dissolved in 500 ml of ligroine, was displaced with 1.5 grams of palladium catalyst (3% on carbon) and 1400 ml isopropanol in a three-liter stirring pressure reactor vessel and hydrogenized and worked in the manner set out in Example 1. The yield of trimethylhydroquinone so produced was 293 grams, corresponding to 96.4% of theoretical and the melting point thereof was 169°–170°C.

EXAMPLE 8

2, 3, 6-trimethylphenol was dissolved in toluene and sulfonated by addition of concentrated sulfuric acid to the solution in dropwise form and stirring phenolsulfonic acid precipitated in solid form from the solution. A further addition of diluted sulfuric acid to the liquid caused redissolving of the solid phenolsulfonic acid therein. The redissolved phenolsulfonic acid was oxidized by addition of sodium dichromate dissolved in water to the liquid in dropwise form. An organic phase containing the 2, 3, 6-trimethylquinone product produced by oxidation was separated from the liquid and 2 moles of this quinone dissolved in toluene were displaced with 700 ml of methanol and a 1.5 gram of palladium (3% on carbon) catalyst in a two-liter stirring pressure reactor vessel and hydrogenized and worked in accordance with Example 1. The yield was 260 grams, equal to approximately 90% in reference to 95% phenol and the melting point of the end product was 169°-170°C.

EXAMPLE 9

A solution of 136 grams (1 mole) of 2, 3-dimethylquinone, dissolved in 250 ml of toluene, was displaced with 350 ml of methanol and 1.0 gm. rhodium catalysts (3% on aluminum oxide carrier) and hydrogenized and worked according to the procedure of Example 1. The yield of the 2, 3-dimethylhydroquinone thus obtained was 132 grams, equalling approximately 95.5% of theoretical yield, and the product melting point was 218°-220°C.

The following examples are similarly processed as in Example 1.

Example 10:
starting material: 2,5-dimethylquinone (1 gram mole)
solvent: 250 ml toluene
displaced by: 350 ml methanol
catalyst: 1.5 gm palladium (2.5% on charcoal)
end product yield: 130 gm (93.5% theoretical)
melting point: 211-213°C.

Example 11:
starting material: 2-methyl-5-isopropyl-quinone (1 gram mole)
solvent: 250 ml benzene
displaced by: 350 ml methanol
catalyst: 1.5 gm ruthenium (5% on charcoal)
end product yield: 159 gm (95.8% theoretical)
melting point: 137-138°C.

Example 12:
starting material: 2,5-di-tert.-tritylguinone (1 gram mole)
solvent: 250 ml toluene
displaced by: 350 ml methanol
catalyst: 1.0 gm rhodium (3% on aluminum oxide)
end product yield: 213 gm (96% theoretical)
melting point: 210-212°C.

Example 13:
starting material: 2-methyl-6 ethyl-quinone (1 gram mole)
solvent: 250 ml toluene
displaced by: 350 ml methanol
catalyst: 2.0 gm platinum (5% on charcoal)
end product yield: 144 gm (94.7% theoretical)
melting point: 98-100°C.

Example 14:
starting material: 2,5-dimethyl-3-ethylquinone (1 gram mole)
solvent: 250 ml benzene
displaced by: 400 ml methanol
catalyst: 1.5 gm palladium (3% on charcoal)
end product yield: 158 gm (95.2% theoretical)
melting point: 160-162°C.

Example 15:
starting material: 2,3,5,6-tetramethylquinone (1 gram mole)
solvent: 250 ml toluene
displaced by: 400 ml methanol
catalyst: 1 gm ruthenium (5% on charcoal)
end product yield: 159 gm (95.8% theoretical)
melting point: 226-227°C.

as used herein "%" refers to theoretical value unless otherwise indicated.

We have therefore described in several embodiments a new process which enables the economic production of substituted hydroquinones in high yields through catalytic hydrogenation of their corresponding quinones. Those skilled in the art, once given the benefit of the foregoing disclosure can make additional variations and uses of the herein described process. It is therefore intended that the foregoing disclosure shall be read as illustrative and not in a limiting sense and that the invention is limited only in accordance with the scope and spirit of the appended claims.

What is claimed is:

1. Process for the production of n-methyl hydroquinone comprising the catalytic hydrogenation of the corresponding n-methyl quinone, $n$ being in each case 1-4, at 1-50 atmospheres pressure and at a temperature no greater than 60°C. in the presence of a mixture of two liquid components, each of which is present in the mixture in an effective amount to modify the effect of the other component, comprising:

as a first component, a $C_1$-$C_3$ alkanol,
as a second component, a hydrocarbon selected from the class consisting of aromatic, aliphatic, and cycloaliphatic hydrocarbons which are inert and are fluid under the hydrogenation reaction conditions,
and wherein the volume ratio of the two components of said mixture is from 1:1 to 1:2.0 between 0° and 60°C.

2. Process in accordance with claim 1 wherein the process is initiated essentially at room temperature and pressure.

3. Process in accordance with claim 1 wherein the alkanol is selected from the class consisting of methanol, ethanol and propanol.

4. Process in accordance with claim 3 wherein the inert hydrocarbon is selected from the class consisting of toluene, benzene, hexane, cyclohexane, and ligroine.

5. Process in accordance with claim 4 wherein said formulation in the respective volume ratios as follows:

|  | Methanol | Ethanol | Propanol | Isopropanol |
|---|---|---|---|---|
| Toluene | 1:1 | 1:1.45 | 1:1.7 | 1:1.45 |
| Benzene | 1:1 | 1:1.45 | 1:1.7 | 1:1.45 |
| Hexane | — | 1:1.45 | 1:2.0 | 1:2.0 |
| Cyclohexane | — | 1:1.45 | 1:2.0 | 1:1.85 |
| Ligroine | — | 1:1.45 | 1:2.3 | 1:2.0. |

6. Process in accordance with claim 1 wherein $n$ is 3.
7. Process in accordance with claim 6 wherein the nucleus is substituted by methyl groups at the 2-, 3-, and 5-positions.
8. Process in accordance with claim 1 wherein $n$ is 2.
9. Process in accordance with claim 1 wherein $n$ is 4.
10. Process in accordance with claim 1 wherein the quinone and hydroquinone are ethyl substituted at least in part.

11. Process in accordance with claim 1 wherein the quinone and hydroquinone are isopropyl substituted.

12. Process in accordance with claim 1 wherein the quinone and hydroquinone are butyl substituted.

13. Process in accordance with claim 5 wherein the quinone is produced in solution and directly hydrogenated without intermediate precipitation from said solution.

14. Process in accordance with claim 5 and further comprising separating catalyst from the reagents and reaction products after completion of hydrogenation, and then precipitating the hydroquinone therefrom.

15. Process in accordance with claim 14 when water is added to said reaction products to precipitate hydroquinone.

16. Process in accordance with claim 14 wherein 0.5% sodium sulfite solution is added to said reaction products to precipitate hydroquinone therefrom.

17. Process in accordance with claim 14 wherein said hydrocarbon is removed from the reaction products and reuse in quinone production.

18. Process in accordance with claim 1 wherein the volume ratio relationship of inert hydrocarbon solvent to alcohol is selected so that the resulting reaction product of hydrogenation remains disolved in the solvent mixture and further comprising, removing catalysts from said solvent mixture containing the reaction products, and subsequently precipitating the hydroquinone from said solvent mixture containing the reaction products.

* * * * *